US008017785B2

(12) United States Patent
Ericsson et al.

(10) Patent No.: US 8,017,785 B2
(45) Date of Patent: Sep. 13, 2011

(54) SALT FORMS OF (2S)-(4E)-N- METHYL-5-[3-(5-ISOPROPOXYPY RIDIN) Y1]-4-PENTEN 2-AMINE

(75) Inventors: Caroline Ericsson, Eslov (SE); Martin Bohlin, Sodertalje (SE); Tesfai Sebhatu, Sodedrtalje (SE); Gary M. Dull, Lewisville, NC (US); Julio A. Munoz, Walnut Cove, NC (US); Craig H. Miller, Winston-Salem, NC (US)

(73) Assignees: AstraZeneca AB, Sodertalje (SE); Targacept, Inc., Winston-Salem, NC (US)

( * ) Notice: Subject to any disclaimer, the term of this patent is extended or adjusted under 35 U.S.C. 154(b) by 0 days.

(21) Appl. No.: 12/299,925

(22) PCT Filed: May 8, 2007

(86) PCT No.: PCT/US2007/068452
§ 371 (c)(1),
(2), (4) Date: May 22, 2010

(87) PCT Pub. No.: WO2007/134038
PCT Pub. Date: Nov. 22, 2007

(65) Prior Publication Data
US 2010/0249196 A1 Sep. 30, 2010

Related U.S. Application Data

(60) Provisional application No. 60/746,808, filed on May 9, 2006.

(51) Int. Cl.
*A61P 25/18* (2006.01)
*A61P 29/28* (2006.01)
*A61P 25/00* (2006.01)

(52) U.S. Cl. .................. 546/300; 514/351; 544/310

(58) Field of Classification Search .................. None
See application file for complete search history.

(56) References Cited

U.S. PATENT DOCUMENTS

| | | | |
|---|---|---|---|
| 4,192,946 A | 3/1980 | Clauson-Kaas et al. |
| 4,487,607 A | 12/1984 | Rose et al. |
| 4,582,823 A | 4/1986 | Heffner et al. |
| 4,922,901 A | 5/1990 | Brooks et al. |
| 5,013,753 A | 5/1991 | Casagrande et al. |
| 5,073,547 A | 12/1991 | Casagrande et al. |
| 5,187,166 A | 2/1993 | Kikuchi et al. |
| 5,212,188 A | 5/1993 | Caldwell et al. |
| 5,583,140 A | 12/1996 | Bencherif et al. |
| 5,597,919 A | 1/1997 | Dull et al. |
| 5,604,231 A | 2/1997 | Smith |
| 5,616,707 A | 4/1997 | Crooks et al. |
| 5,616,716 A | 4/1997 | Dull et al. |
| 5,663,356 A | 9/1997 | Ruecroft et al. |
| 5,672,601 A | 9/1997 | Cignarella |
| 5,726,316 A | 3/1998 | Crooks |
| 5,811,442 A | 9/1998 | Bencherif et al. |
| 5,852,041 A | 12/1998 | Cosford et al. |
| 5,861,423 A | 1/1999 | Caldwell |
| 6,232,316 B1 * | 5/2001 | Dull et al. ..................... 514/256 |
| 6,337,351 B1 | 1/2002 | Dull et al. |
| 6,432,954 B1 | 8/2002 | Dull et al. |
| 6,492,399 B1 | 12/2002 | Dull et al. |
| 6,599,897 B1 | 7/2003 | Brown |
| 6,603,011 B1 | 8/2003 | Caldwell et al. |
| 6,632,823 B1 | 10/2003 | Vernier et al. |
| 6,743,812 B1 | 6/2004 | Dull |
| 6,958,399 B2 | 10/2005 | Caldwell et al. |
| 7,459,469 B2 | 12/2008 | Munoz et al. |
| 2002/0016460 A1 | 2/2002 | Snow et al. |
| 2002/0052497 A1 | 5/2002 | Caldwell et al. |
| 2003/0069272 A1 | 4/2003 | Yerxa et al. |
| 2004/0044023 A1 | 3/2004 | Cantillon et al. |
| 2004/0067974 A1 | 4/2004 | Czollner et al. |
| 2005/0203130 A1 | 9/2005 | Buntinx |
| 2006/0024358 A1 | 2/2006 | Santini et al. |
| 2006/0062838 A1 | 3/2006 | Dipierro et al. |
| 2006/0122237 A1 | 6/2006 | Munoz et al. |
| 2006/0122238 A1 | 6/2006 | Dull et al. |
| 2006/0159768 A1 | 7/2006 | Brown |
| 2007/0265314 A1 | 11/2007 | Dull et al. |
| 2008/0085888 A1 | 4/2008 | Breining et al. |
| 2008/0249142 A1 | 10/2008 | Dull et al. |
| 2009/0062321 A1 | 3/2009 | Munoz et al. |

FOREIGN PATENT DOCUMENTS
EP 0297858 1/1989
(Continued)

OTHER PUBLICATIONS

Bastin et al., Salt Selection and Optimisation Procedures for Pharmaceutical New Chemical Entities, 4 Org. Process Res. & Dev. 427-35 (2000).*
Berge et al., Pharmaceutical Salts, 66 (1) J. Pharma. Sci., 1-19 (Jan. 1977).*
Supplemental Notice of Allowability for co-pending U.S. Appl. No. 11/270,753 dated May 16, 2008.
Notice of Allowance for co-pending U.S. Appl. No. 11/270,753 dated Oct. 24, 2008.
Official Action for co-pending U.S. Appl. No. 11/745,682 dated Dec. 11, 2009.
Bastin et al., "Salt selection and optimization for pharmaceutical new chemical entitles," Organic Process Research and Development (2000) 4(5):427-435.
Final Office Action received in copending U.S. Appl. No. 11/745,682 dated May 3, 2010.
de Costa et al., "Synthesis and biological evaluation of conformationally restricted 2-(1-pyrrolidinyl)-N-[2-(3,4-dichlorophenyl)ethyl]-N-methylethylenediam ines as sigma receptor ligands. 1. Pyrrolidine, piperidine, homopiperidine, and tetrahydroisoquinoline classes," J med Chem (1992) 35(23):4334-4343.

(Continued)

Primary Examiner — Janet Andres
Assistant Examiner — Timothy R Rozof

(57) ABSTRACT

Phosphoric acid, edisylic acid (1,2-ethanedisulfonic acid), citric acid, orotic acid (uracil-6-carboxylic acid), R-mandelic acid, sulfuric acid, 1,5-naphthalenedisulfonic acid, D-aspartic acid, and lysine monohydrochloride salts of (2S)-(4E)-N-methyl-5-[3-(5-isopropoxypyridin)yl]-4-penten-2-amine, and methods for their preparation, pharmaceutical compositions comprising said salts, and use, are disclosed. The salts can be administered to patients susceptible to or suffering from conditions and disorders, such as central nervous system disorders, to treat and/or prevent such disorders.

4 Claims, No Drawings

FOREIGN PATENT DOCUMENTS

| | | |
|---|---|---|
| EP | 0516409 | 12/1992 |
| GB | 2295387 | 5/1996 |
| JP | 2002518373 | 6/2002 |
| JP | 2008519768 | 6/2008 |
| WO | 9212122 | 7/1992 |
| WO | 9408992 | 4/1994 |
| WO | 9534555 | 12/1995 |
| WO | 9631475 | 10/1996 |
| WO | 9640682 | 12/1996 |
| WO | 9740011 | 10/1997 |
| WO | 9850367 | 11/1998 |
| WO | 9921834 | 5/1999 |
| WO | 9965876 | 12/1999 |
| WO | 0007600 | 2/2000 |
| WO | 2004/031151 A1 | 8/2000 |
| WO | 0075110 | 12/2000 |
| WO | 0117943 | 3/2001 |
| WO | 0178735 | 10/2001 |
| WO | 0205801 | 1/2002 |
| WO | 0205801 A2 | 1/2002 |
| WO | 02078693 | 10/2002 |
| WO | 03051302 | 6/2003 |
| WO | 03082205 | 10/2003 |
| WO | 2005/072742 A1 | 4/2004 |
| WO | 2005063296 A2 | 7/2005 |
| WO | 00/45846 A1 | 8/2005 |
| WO | 2005105729 | 11/2005 |
| WO | 2006053039 | 5/2006 |
| WO | 2006053039 A2 | 5/2006 |
| WO | 2006053082 | 5/2006 |
| WO | 2006011440 | 11/2006 |
| WO | 2007134034 | 11/2007 |
| WO | 2007134038 | 11/2007 |
| WO | 2007147014 A2 | 12/2007 |
| WO | 2008034041 | 3/2008 |
| WO | 2008073942 | 6/2008 |
| WO | 2008091588 | 7/2008 |
| WO | 2008091592 | 7/2008 |

OTHER PUBLICATIONS

Koller et al., "The Preparation of Substituted Hydroxyphenyl-pyridyl-ethanols and -Hydroxyphenyl—methylpyridineethanols by the Condensation of 2-, 3-, or 4-Picolyllithium with Select Hydroxybenzaldehydes and 4-Hydroxyacetophenone," Synthetic Communications (1995) 25(19):2963-2974.

Acheson et al., "Transformations involving the Pyrrolidine Ring of Nicotine," J Chem Soc (1980) 1:579-585.

Arneric et al., "Cholinergic channel modulators as a novel therapeutic strategy for Alzheimer's disease," Exp Opin Invest Drugs (1996) 5(1):79-100.

Arneric et al., "Preclinical Pharmacology of ABT-418: A Prototypical Cholinergic Channel Activator for the Potential Treatment of Alzheimer's Disease," CNS Drug Rev (1995) 1(1):1-26.

Ashimori et al., "Novel 1, 4-Dihydropyride Calcium Antagonists. I. Synthesis and Hypotensive Activity of 4-(Substittuted Pyridyl)-1,4-dihydropyridine Derivatives,," Chem. Pharm Bull (1990) 38(9):2446-2458.

Bannon et al., "Broad-Spectrum, Non-Opioid Analgesic Activity by Selective Modulation of Neuronal Nicotinic Acetylcholine Receptors," Science (1998) 279:77-81.

Batkowski, Rocz Chem (1967) 41:729-741.

Bencherif et al., "Targeting Neuronal Nicotinic Receptors: a Path to New Therapies," Current Drug Targets (2002) 1 (4):349-357.

Bencherif et al., "RJR-2403: A Nicotinic Agonist with CNS Selectivity I: In Vitro characterization," J Pharmacol Exper Therapeutics (1996) 279(3):1413-1421.

Borch "Reductive Amination with Sodium Cyanoborohydride: N, N-Dimethylcyclohexyl," Org Syn (1974) 52:124-127.

Brioni et al., "The harmacology of (−)-Nicotine and Novel Cholinergic channel Modulators," Adv Pharmacol (1997) 37:153-214.

Cai et al., "5-(N-Oxyaza-7-substituted-1,4-dihydroquinoxaline-2,3-diones: Novel, Systemically Active and Broad Spectrum An," J Med Chem (1997) 40(22):3679-3686.

Cheng et al., "Relationship Between the Inhibition Constant (KI) and the Concentration of Inhibitor which Causes 50 Per Cent inhibition (I50) of an Enzymatic Reaction," (1973) Biochem Pharmacol (1973) 22(23):3099-3108.

Chiari et al., "Sex Differences in Cholinergic Analgesia I: A Supplemental Nicotinic Mechanism in Normal Females," (1999) Anesthesiology 91(5):1447-1454.

Comins et al., "Lithiation of Methoxypyridines Directed by beta-Amino Alkoxides," (1990) J Org Chem 91(5):69-73.

Dallacker et al., "," Naturforsch (1979) 34b:1729-1736.

Damaj et al., "Analgesic Activity of Metanicotine, A Selective Nicotinic Agonist," Neuroscience (1997) 23:669.

Damaj et al., "Antinociceptive and Pharmacological Effects of Metanicotine, a Selective Nicotinic Agonist," J Pharmacol Exp Ther (1999) 291(1):390-398.

Decina et al., "Cigarette Smoking and Neuroleptic-Induced Parkinsonism," Biol Psychiatry (1990) 28(6):502-508.

Dubey et al., "Synthesis & Spectra of 2-Alkyl—& 6-Bromo-2-alkyl-1H-imidazo[b]pyridines," Indian J Chem (1978) 16B (6):531-533.

Dwoskin et al., "Recent developments in neuronal nicotinic acetylcholine receptor antagonists," Exp Opin Ther Patents (2000) 10(10):1561-1581.

Frank et al., "Palladium-Catalyzed Vinylic Substitution Reactions with Heterocyclic Bromides," J Org Chem (1978) 43 (15):2947-2949.

Frissen et al., "Ring-Transformations of Pyrimidines by Intramolecular Diels-Alder Reactions, Sythesis of Annelated Pyridines," Tetrahedron (1989) 45(3):803-812.

Gibson et al., "Principal Components Describing biological Activities and Molecular Diversity of Heterocyclic Aromatic Ring Fragments," J Med Chem (1996) 39:4065-4072.

Greco et al., "Synthese of Some Substituted Pyridylsydnones," J Heterocyclic Chem (1970) 7:761-766.

Hall et al., "Effects of Nicotine on the Release of 3H-Noradrenaline from the Hypothalamus," Biochemical Pharmacology (1972) 21:1829-1838.

Hamon "Neuropharmacology of anxiety: perspectives and prospects," TIPS (1994) 15:36-39.

Harsing et al., "Dopamine Efflux from Striatun After Chronic Nicotine: Evidence for Autoreceptor Desensitization," J Neurochem (1992) 59(1):48-54.

Hayes et al., Elimination of Dihydrogen from Collision-activated Alkoxide Negative Ions in the Gas Phase. An Ab inition and Isotope Effect Study, J Chem Soc Chem Commun (1984) 21:1431-1432.

Hertog et al., "The Reactivity of Bromine Atoms in Brominated Pyridines," Recl Trav Chim Pays-Bas (1948) 67 (7/8):377-379.

Hery et al., "Control of the release of newly synthetized 3H-5-Hydroxytryptamine by Nicotinic and Muscarinic Receptors in Rat Hypothalamic Slices," Naunyn-Schmiedeberg's Arch Pharmacol (1977) 296:91-97.

Holladay et al., "Neuronal Nicotinic Acetylcholine Receptors as Targets for Drug Discovery," J Med Chem (1997) 40 (26):4169-4194.

Hoyer et al., "Partial agonists, full agonists, antagonists: dilemmas of definition," TIPS Reviews (1993) 14:270-275.

Hughes et al., "S 40 Nicitine and Neuropsychiatric Disorders," Session 6, in International Symposium on Nicotine: The Effects of Nicotine on Biological Systems II, (Birkhauser Verlag Publishers, 1994).

Ishihara et al., "Zinc Bromide Promoted Allylatin of Aluminum Acetals Derived from Perfluoro Carboxylic Acid Esters and Diisobutylaluminum Hybride," Tetrahedron Letters (1993) 34(36):5777-5780.

Kalivretenos et al., "Synthesis of Beta-Resocylic Macrolides via Organopalladium Chemistry Application to the Total Synthesis of (S)-Zearalenone," J Org Chem (1991) 56:2883-2894.

Koch et al., "Chemistry of 3-Hydroxypyridine Part 2: Synthesis of 5,6-Dihalo-3-hydroxypyriines," Synthesis (1990) 499-501.

Kubota et al., "Facile Synthesis of Beta-Trifluoromethlated Alcohols from Trifluoroacetaldehyde Ethyl Hemiacetal," Tetrahedron Letters (1992) 33(10):1351-1354.

Kuhler et al., "Structure-Activity Relationship of Omeprazole and Analogues as Helicobacter pylorie Urease Inhibitors," J Med Chem (1995) 38:4906-4916.

LaForge "The preparation and properties of some new derivatives of pyridine," J Am Chem Soc (1928) 50:2477-2483.

Lavand'homme et al., "Sex Differences in Cholinergic Analgesia II: differing Mechanisms in Two Models of Allodynia," Anesthesiology (1999) 91(5):1455-1461.

Levin et al., "Nicotinic treatment for cognitive dysfunction," Current Drug Targets: CNS and Neurological Disorders (2002) 1(4):423-431.

Lippiello et al., "RJR-2403: a nicotinic agonist with CNS selectivity II. In vivo characterization," J Pharmacol Exp Ther (1996) 279(3):1422-1429.

Loffer et al., "[Uber die bildung des i-nicotins aus N-methyl-b-pyridyl-butyl-amin (dihydrometanicotin)]," Chem Ber (1909) 42:3431-3438.

Malek et al., "Palladium-catalyzed synthesis of cinnamylamines," J Org Chem (1982) 47:5395-5397.

Michael et al., "Synthesis of functionalized cyclopentanes, cyclohexanes and cycloheptanes by a silicon-induced domino reaction," Liebigs Ann (1996) 11:1811-1821.

Morisawa et al., "Modification at 5-position of 4-deoxypyridoxol and alpha4-norpyridoxol," Agr Biol Chem (1975) 39 (6):1275-1281.

Onaivi et al., "Chronic nicotine reverses age-associated increases in tail-flick latency and anxiety in rats," Life Sciences (1993) 54(3):193-202.

Toth et al., "Effect of nicotine of extracellular levels of neurotransmitters assessed by microdialysis in various brain regions: role of glutamic acid," Neurochem Res (1992) 17(3):265-270.

Tripathi et al., "Nicotine-induced antinociception in rats and mice: correlation with nicotine brain levels," J Pharmacol Exp Ther (1982) 221(1):91-96.

Viaud et al., "Synthesis of 6-substituted 2-phenyloxazolo-[4,5-b] pyridines," Heterocycles (1995) 41(12):2799-2809.

Vizi et al., "Acetylcholine release from guinea-pig ileum by parasympathetic ganglion stimulants and gastrin-like polypeptides," Br J Pharmac (1973) 47(4):765-777.

Wagner et al., "Does smoking reduce the risk of neuroleptic parkinsonoids?" Pharmacopsychiat (1988) 21:302-303.

Williams et al., "Neuronal nicotinic acetylcholine receptors," Drug News Perspec (1994) 7(4):205-223.

Yoshikawa et al., "Synthesis of 3-pyridinols. II. Reaction of 4-methyloxazole with dienophiles," Chem Pharm Bull (1965) 13(7):873-878.

Bibliographic printout from DIALOG research company (corresponding to Japanese Patent No. 70012732).

Office Action dated Jan. 7, 2008 cited in copending U.S. Appl. No. 11/270,018.

Notice of Allowance dated Apr. 8, 2008 cited in copending U.S. Appl. No. 11/270,753.

Geerts "Ispronicline Targacept," Current Opinion in Investigational Drugs (2006) 7(1):60-69.

Buccafusco "Neuronal nicotinic receptor subtypes: defining therapeutic targets," Molecular Interventions (2004) 4 (5):285-295.

Haberman "Nicotinic receptor agonists for treating diseases of cognitive dysfunction," Spectrum (2007) pp. 11-1 to 11-19.

Notice of Allowance for co-pending U.S. Appl. No. 11/270,018 dated Aug. 4, 2008.

Office Action for co-pending U.S. Appl. No. 11/855,175 dated Nov. 13, 2008.

Gould "Salt selection for basic drugs," International Journal of Pharmaceutics (1986) 33:201-217.

Bastin, et al., Salt Selection and Optimization for Pharmaceutical New Chemical Entities, Organic Process Research and Development, 2000; 4(5):427-435.

Levin, et al., Nicotine-Haloperidoal Interactions and Cognitive Performance in Schizophrenics, Neuropsychopharmacology, 1996;15(5):429-436.

Ichikawa, et al., Atypical antipsychotic drugs, quetiapine, iloperidone, and melperone, preferentially increase dopamine and acetylcholine release in rat medial prefrontal cortex: role of 5-HT1A receptor agonism, Brain Research (2002) 956:349-357.

Shoemaker, et al., Quetiapine produces a prolonged reversal of the sensorimotor gating-disruptive effects of basolateral amygdala lesions in rats, Behavioral Neuroscience (2003) 117(1):136-143.

Letchworth et al., "Tc-1734: an orally active neuronal nicotinic receptor modulator with long-lasting cognitive effects, anti-depressant effects, and neuroprotective activity," Society for Neuroscience (2003) Abstract.

Advisory action dated Oct. 8, 2010 received in copending U.S. Appl. No. 11/745,682.

Canney et al., "Characterization of ethyl (3-quinuclidinyl) acetate (EQA) as a ligand for acetylcholine receptors," Life Sciences (1998) 63(24):PL329-PL336.

Non-final office action dated Jan. 14, 2011 received in copending U.S. Appl. No. 12/264,288.

O'Neill et al., "The role of neuronal nicotinic acetylcholine receptors in acute and chronic neurodegeneration," Current Drug Targets: CNS and Neurological Disorders (2002) 1(4):399-411.

Paulder et al., "1,2,4-Triazines. III. A convenient synthesis of 1,2,4-triazines and their covalent hydration," J Heterocyclic Chem (1970) 7:767-771.

Pomerleau et al., "The effects of cigarette smoking on pain and anxiety," Addictive Behaviors (1984) 9(3):265-271.

Pullan et al., "Transdermal nicotine for active ulcerative colitis," New England J Med (1994) 330(12):811-815.

Rapier et al., "Stereoselective nicotine-induced release of dopamine from striatal synaptosomes: concentration dependence and repetitive stimulation," J Neurochem (1988) 50(4):1123-1130.

Rondahl "Synthetic analogues of nicotine VI1,2. Nicotine substituted in the 5-position," Acta Pharmaceutica Suecica (1977) 14(2):113-118.

Rowell et al., "Nicotinic stimulation of [3H]acetylcholine release from mouse cerebral cortical synaptosomes," J Neurochem (1984) 43 (6):1593-1598.

Sanberg et al., "Nicotine potentiation of haloperidol-induced catalepsy: striatal mechanisms," Pharmacol Biochem & Behavior (1993) 46(2):303-307.

Sandor et al., "Effect of nicotine on dopaminergic-cholinergic interaction in the striatum," Brain Res (1991) 567 (2):313-316.

Sjak-Shie et al., "Effects of chronic nicotine and pilocarpine administration on neocortical neuronal density and [3H] GABA uptake in nucleus basalis lesioned rats," Brain Res (1993) 624:295-298.

Schmitt et al., "Chapter 5. Targeting nicotinic acetylcholine receptors: advances in molecular design and therapies," Ann Rep Med Chem (2000) 35:41-51.

Taylor et al., "Intramolecular diels-alder reactions of 1,2,4-triazines. A general synthesis of furo[2,3- ]pyridines, 2,3-dihydropyrano[2,3- ] pyridines, and pyrrolo[2,3- ]pyridines," Tetrahedron (1987) 43(21):5145-5158.

Grottick et al., "Effect of subtype selective nicotinic compounds on attention as assessed by the five-choice serial reaction time task," Behav Brain Res. (2000) 117:197-208.

* cited by examiner

US 8,017,785 B2

SALT FORMS OF (2S)-(4E)-N-METHYL-5-[3-(5-ISOPROPOXYPYRIDIN)Y1]-4-PENTEN 2-AMINE

CROSS-REFERENCE TO RELATED APPLICATIONS

This application is the U.S. National Stage filing of International Application Serial No. PCT/SE2007/068452 filed May 8, 2007, which claims priority to U.S. Provisional Application No. 60/746,808 filed May 9, 2006, each of which is incorporated herein by reference in its entirety.

FIELD OF THE INVENTION

The present invention relates to novel salt forms of (2S)-(4E)-N-methyl-5-[3-(5-isopropoxypyridin)yl]-4-penten-2-amine, as well as pharmaceutical compositions including the salt forms. The present invention also relates to methods for treating a wide variety of conditions and disorders, and particularly conditions and disorders associated with dysfunction of the central and autonomic nervous systems, using the novel salt forms.

BACKGROUND OF THE INVENTION

The compound (2S)-(4E)-N-methyl-5-[3-(5-isopropoxypyridin)yl]-4-penten-2-amine is known to provide benefits in the area of the treatment and/or prevention of central nervous system disorders. The compound, its synthesis, and its use in methods of medical treatment, is described, for example, in PCT WO 99/65876 to Caldwell et al. and in U.S. application Ser. No. 11/270,018, the contents of which are hereby incorporated by reference in their entirety.

The commercial development of a drug candidate such as (2S)-(4E)-N-methyl-5-[3-(5-isopropoxypyridin)yl]-4-penten-2-amine involves many steps, including scaling up the chemical synthesis and purification, finding optimal salt forms, and the like.

In the formulation of drug compositions, it is important for the drug substance to be in a form in which it can be conveniently handled and processed. This is of importance, not only from the point of view of obtaining a commercially-viable manufacturing process, but also from the point of view of subsequent manufacture of pharmaceutical formulations comprising the active compound.

Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility). Moreover, it is also important to be able to provide drug in a form, which is as chemically pure as possible.

The skilled person will appreciate that, typically, if a drug can be readily obtained in a stable form, such as a stable crystalline form, advantages may be provided, in terms of ease of handling, ease of preparation of suitable pharmaceutical compositions, and a more reliable solubility profile.

SUMMARY OF THE INVENTION

The present invention relates to a phosphoric acid, edisylic acid (1,2-ethanedisulfonic acid), citric acid, orotic acid (uracil-6-carboxylic acid), R-mandelic acid, sulfuric acid, 1,5-naphthalenedisulfonic acid, D-aspartic acid, or lysine monohydrochloride salt of (2S)-(4E)-N-methyl-5-[3-(5-isopropoxypyridin)yl]-4-penten-2-amine. These phosphoric acid and edisylic acid salts can be obtained in either amorphous or crystalline forms. The invention also relates to the preparation of these salts. In one embodiment, the stoichiometric ratio of the acid to the amine is 1:1 or 1:2.

The present invention also relates to methods for treating and/or preventing a wide variety of conditions or disorders, and particularly those disorders characterized by dysfunction of nicotinic cholinergic neurotransmission including disorders involving neuromodulation of neurotransmitter release, such as dopamine release. The present invention also relates to methods for treating and/or preventing disorders, such as central nervous system (CNS) disorders, which are characterized by an alteration in normal neurotransmitter release, and also for treating certain conditions (e.g., alleviating pain). The methods involve administering to a subject an effective amount of the novel salt forms, or pharmaceutical compositions including such salt forms.

The salt forms can be provided in the form of a pharmaceutical composition that includes an effective amount of the salt forms described herein. The pharmaceutical compositions incorporate a salt form of (2S)-(4E)-N-methyl-5-[3-(5-isopropoxypyridin)yl]-4-penten-2-amine, which, when employed in effective amounts, interacts with relevant nicotinic receptor sites of a subject, and hence has acts as a therapeutic agent to treat and prevent a wide variety of conditions and disorders, particularly those disorders characterized by an alteration in normal neurotransmitter release.

The pharmaceutical compositions provide therapeutic benefit to individuals suffering from such disorders and exhibiting clinical manifestations of such disorders in that the compounds within those compositions, when employed in effective amounts, (i) exhibit nicotinic pharmacology and affect relevant nicotinic receptors sites (e.g., act as a pharmacological agonist to activate nicotinic receptors), and/or (ii) elicit neurotransmitter secretion, and hence prevent and suppress the symptoms associated with those diseases.

In addition, the compounds have the potential to (i) increase the number of nicotinic cholinergic receptors of the brain of the patient, (ii) exhibit neuroprotective effects and/or (iii) when employed in effective amounts, do not cause appreciable adverse side effects (e.g., significant increases in blood pressure and heart rate, significant negative effects upon the gastro-intestinal tract, and significant effects upon skeletal muscle).

The pharmaceutical compositions are believed to be safe and effective with regards to prevention and treatment of a wide variety of conditions and disorders.

The foregoing and other aspects of the present invention are explained in detail in the detailed description and examples set forth below.

DETAILED DESCRIPTION

The salt forms of (2S)-(4E)-N-methyl-5-[3-(5-isopropoxypyridin)yl]-4-penten-2-amine, pharmaceutical compositions including these salt forms, methods of preparing the salt forms, and methods of treatment and/or prevention using the salt forms, are described in detail below.

As used herein, the terms "salt forms" and "compounds" each refer to the salt forms of (2S)-(4E)-N-methyl-5-[3-(5- isopropoxypyridin)yl]-4-penten-2-amine, unless, in that particular context, it is clear that the compound being referred to is the free base itself.

I. (2S)-(4E)-N-METHYL-5-[3-(5-ISOPROPOXY-PYRIDIN)YL]-4-PENTEN-2-AMINE

The compounds described herein are phosphoric acid, edisylic acid (1,2-ethanedisulfonic acid), citric acid, orotic acid (uracil-6-carboxylic acid), R-mandelic acid, sulfuric acid, 1,5-naphthalenedisulfonic acid, D-aspartic acid, and lysine monohydrochloride salts of (2S)-(4E)-N-methyl-5-[3-(5-isopropoxypyridin)yl]-4-penten-2-amine, which has the formula:

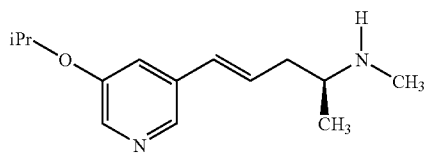

The manner in which the (2S)-(4E)-N-methyl-5-[3-(5-isopropoxypyridin)yl]-4-penten-2-amine and its salts can be prepared can vary. Approaches for preparing (2S)-(4E)-N-methyl-5-[3-(5-isopropoxypyridin)yl]-4-penten-2-amine are described, for example, in PCT WO 99/65876 to Caldwell et al. and in U.S. application Ser. No. 11/270,018, pertinent portions of which are summarized below.

One synthetic approach involves a convergent synthesis, in which the side chain, (2S)—N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The (2S)—N-methyl-N-(tert-butoxycarbonyl)-4-penten-2-amine can be synthesized as follows: (i) (2R)-4-Penten-2-ol can be prepared from (R)-(+)-propylene oxide, according to procedures set forth in A. Kalivretenos, J. K. Stille, and L. S. Hegedus, *J. Org. Chem.* 56: 2883 (1991), and then treated with p-toluenesulfonyl chloride in pyridine to yield (2R)-4-penten-2-ol p-toluenesulfonate. (ii) The resulting tosylate can be heated with 20 molar equivalents of methylamine (as a 40% aqueous solution) in dimethylformamide to yield (2S)—N-methyl-4-penten-2-amine. (iii) The resulting amine can be allowed to react with di-tert-butyl dicarbonate in ether to yield the side chain, (2S)—N-methyl-N-(tert-butoxycarbonyl)-4-penten-2-amine.

The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and (2S)—N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (2S)-(4E)-N-methyl-N-(tert-butoxycarbonyl)-5-(5-isopropoxy-3-pyridyl)-4-penten-2-amine Removal of the tert-butoxycarbonyl protecting group can be accomplished by treatment with 30 molar equivalents of trifluoroacetic acid in anisole at 0° C. to afford (2S)-(4E)-N-methyl-5-(5-isopropoxy-3-pyridyl)-4-penten-2-amine.

II. SALT FORMS OF (2S)-(4E)-N-METHYL-5-[3-(5-ISOPROPOXYPYRIDIN)YL]-4-PENTEN-2-AMINE

The compounds (novel salt forms) described herein are salt compositions that possess anions derived from phosphoric acid, edisylic acid (1,2-ethanedisulfonic acid), citric acid, orotic acid (uracil-6-carboxylic acid), R-mandelic acid, sulfuric acid, 1,5-naphthalenedisulfonic acid, D-aspartic acid, and lysine monohydrochloride, and cations derived from (2S)-(4E)-N-methyl-5-[3-(5-isopropoxypyridin)yl]-4-penten-2-amine. The stoichiometry of the salts comprising the present invention can vary, as discussed below.

Citric acid (2-hydroxypropane-1,2,3-tricarboxylic acid) has three carboxylic acid groups, of varying acid strengths, that can react with one or both of the amine groups present on (2S)-(4E)-N-methyl-5-[3-(5-isopropoxypyridin)yl]-4-penten-2-amine. Accordingly, the acid-base reaction can occur, for example, in a ratio of one citric acid molecule to one, two, or three (2S)-(4E)-N-methyl-5-[3-(5-isopropoxypyridin)yl]-4-penten-2-amine molecules, two citric acid molecules to one, three or five (2S)-(4E)-N-methyl-5-[3-(5-isopropoxypyridin)yl]-4-penten-2-amine molecules, four citric acid molecules to three (2S)-(4E)-N-methyl-5-[3-(5-isopropoxypyridin)yl]-4-penten-2-amine molecules, and so on.

Phosphoric acid ($H_3PO_4$) also has three acidic protons of varying acid strengths. The phosphate salts can be present in the same stoichiometric ratios as the citric acid salts. 1,2-Ethanedisulfonic acid has two carboxylic acid groups. The ratios between 1,2-ethanedisulfonic acid and (2S)-(4E)-N-methyl-5-[3-(5-isopropoxypyridin)yl]-4-penten-2-amine can also vary, to the extent that one molecule of the acid can react with two molecules of the base, two molecules of the acid can react with one molecule of the base, or one molecules of the acid can react with one molecule of the base, giving rise to stoichiometries of acid/base of 1:1, 1:2, and 2:1.

Sulfuric acid, 1,5-naphthalenedisulfonic acid, D-aspartic acid, and lysine hydrochloride each have two acidic protons of varying acid strengths. Salts of each of these can exist in the same stoichiometric ratios as 1,2-ethanedisulfonic acid salts.

Orotic acid (uracil-6-carboxylic acid) and R-mandelic acid each have one acidic proton and can combine with (2S)-(4E)-N-methyl-5-[3-(5-isopropoxypyridin)yl]-4-penten-2-amine in ratios of 2:1 or 1:1 (acid to base) for instance.

In the presently disclosed salts, it is typical that the molar ratio of acid to base ((2S)-(4E)-N-methyl-5-[3-(5-isopropoxypyridin)yl]-4-penten-2-amine) is 1:2 or 1:1, but other ratios (such as 3:2 and 2:1) are possible.

Depending upon the manner by which the salts described herein are formed, the salts can have crystal structures that occlude solvents that are present during salt formation. Thus, the salts can occur as hydrates and other solvates of varying stoichiometry of solvent relative to the (2S)-(4E)-N-methyl-5-[3-(5-isopropoxypyridin)yl]-4-penten-2-amine.

The method for preparing the salt forms can vary. The preparation of (2S)-(4E)-N-methyl-5-[3-(5-isopropoxypyridin)yl]-4-penten-2-amine salt forms involves:

(i) the free base or a solution of the free base of suitably pure (2S)-(4E)-N-methyl-5-[3-(5-isopropoxypyridin)yl]-4-penten-2-amine in a suitable solvent is mixed with any of the acids in pure form or as a solution of any of the acids in a suitable solvent (typically 0.5 to 1 equivalents of the acid), (iia) cooling the resulting salt solution if necessary to cause precipitation, or (iib) adding a suitable anti-solvent to cause precipitation, or (iic) evaporating the first solvent and adding and new solvent and repeating either steps (iia) or step (iib), and (iii) filtering and collecting the salt.

The stoichiometry, solvent mix, solute concentration and temperature employed can vary. Representative solvents that can be used to prepare and/or recrystallize the salt forms include, without limitation, ethanol, methanol, isopropyl alcohol, acetone, ethyl acetate, and acetonitrile.

According to a further aspect of the invention there is provided the phosphate and edisylate salt of the invention in substantially crystalline form.

Although we have found that it is possible to produce phosphate and edisylate salts of the invention in forms which are greater than 80% crystalline, by "substantially crystalline" we include greater than 20%, preferably greater than 30%, and more preferably greater than 40% (e.g. greater than any of 50, 60, 70, 80 or 90%) crystalline.

According to a further aspect of the invention there is also provided a phosphate and edisylate salt of the invention in partially crystalline form. By "partially crystalline" we include 5% or from 5% to 20% or between 5% and 20% crystalline.

The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

Crystalline (2S)-(4E)-N-methyl-5-[3-(5-isopropoxypyridin)yl]-4-penten-2-amine salts were analyzed using X-ray powder diffraction (XRPD) as described below:

The peaks, identified with d-values calculated from the Bragg formula and intensities, have been extracted from the diffractogram of crystalline salt. Only the main peaks that are the most characteristic, significant, distinct and/or reproducible, have been tabulated, but additional peaks can be extracted, using conventional methods, from the diffractogram. The presence of these main peaks, reproducible and within the error limit, is for most circumstances sufficient to establish the presence of said crystalline salt.

X-ray diffraction analyses were performed using a PANalytical X'Pert Pro MPD diffractometer for 96 minutes from 1 to 60° 2θ with and without internal standard reference. The 2θ angles were corrected with regard to the standard values whereafter calculation into d-values (distance values) was done. The d-values may vary in the range ±2 on the last given decimal place. The sample preparation was performed according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London or Klug, H. P. & Alexander, L. E. (1974), X-ray Diffraction Procedures, John Wiley and Sons, New York.

The term "stability" as defined herein includes chemical stability and solid state stability.

By "chemical stability", we include that it may be possible to store salts of the invention in an isolated form, or in the form of a formulation in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition.

By "solid state stability", we include that it may be possible to store salts of the invention in an isolated solid form, or in the form of a solid formulation in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of from minus 80 to plus 50° C. or between minus 80 and plus 50° C. (preferably from 0 to 40° C. or between 0 and 40° C. and more preferably room temperatures, such as from 15 to 30° C. or between 15 and 30° C.), pressures from 0.1 to 2 bars or between 0.1 and 2 bars (preferably at atmospheric pressure), relative humidities from 5 to 95% or between 5 and 95% (preferably, from 10 to 60%), and/or exposure to 460 lux of UV/visible light, for prolonged periods (i.e. greater than or equal to six months). Under such conditions, salts of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

A further aspect of the present invention comprises processes for the preparation of the salts. The precise conditions under which the salts are formed may be empirically determined The salts may be obtained by crystallisation under controlled conditions.

One embodiment of the invention relates to phosphate salt of (2S)-(4E)-N-methyl-5-[3-(5-isopropoxypyridin)yl]-4-penten-2-amine having an X-ray powder diffraction pattern with specific peaks at d-values at 18.6, 9.3, 4.25, 3.99, and 3.11 Å, and/or essentially as defined in Table 1.

Another embodiment of the invention relates to a edisylate salt of (2S)-(4E)-N-methyl-5-[3-(5-isopropoxypyridin)yl]-4-penten-2-amine having an X-ray powder diffraction pattern with specific peaks at d-values at 5.6, 4.33, 4.19, and 3.76 Å, and/or essentially as defined in Table 2.

III. METHODS OF TREATMENT

The salt forms described herein can be used in methods for preventing and/or treating a condition or disorder in a subject susceptible to such a condition or disorder. For example, an effective amount of a compound effective for providing some degree of prevention of the progression of a CNS disorder (i.e., provide protective effects), amelioration of the symptoms of a CNS disorder, and amelioration of the reoccurrence of a CNS disorder, can be administered to a patient in need thereof.

The compounds can be used to treat and/or prevent those types of conditions and disorders for which other types of nicotinic compounds have been proposed as therapeutics. See, for example, Williams et al. DN&P 7(4):205-227 (1994), Arneric et al., CNS Drug Rev. 1(1):1-26 (1995), Arneric et al., Exp. Opin. Invest. Drugs 5(1):79-100 (1996), Bencherif et al., JPET 279:1413 (1996), Lippiello et al., JPET 279:1422 (1996), Damaj et al., Neuroscience (1997), Holladay et al., J. Med. Chem. 40(28): 4169-4194 (1997), Bannon et al., Science 279: 77-80 (1998), PCT WO 94/08992, PCT WO 96/31475, and U.S. Pat. Nos. 5,583,140 to Bencherif et al., 5,597,919 to Dull et al., and 5,604,231 to Smith et al the disclosures of which are incorporated herein by reference in their entirety.

The compounds modulate nicotinic receptors in the patient's brain. As such, such compounds have the ability to express nicotinic pharmacology, and in particular, to act as nicotinic partial agonists.

Receptor binding constants provide a measure of the ability of the compound to bind to half of the relevant receptor sites of certain brain cells of the patient. See, Cheng, et al., Biochem. Pharmacol. 22:3099 (1973). The (2S)-(4E)-N-methyl-5-[3-(5-isopropoxypyridin)yl]-4-penten-2-amine compound used to prepare the salts has extremely high affinity for the relevant receptors, with a binding affinity in the low nM range.

The compounds have the ability to demonstrate a nicotinic function by effectively modulating neurotransmitter secretion from neurons. As such, such compounds have the ability to affect relevant the release of acetylcholine, dopamine, and other neurotransmitters by neurons.

The compounds, when employed in effective amounts in accordance with the methods described herein, are selective to certain relevant nicotinic receptors, but do not cause significant activation of receptors associated with undesirable side effects at concentrations at least greater than those required for modulation of CNS neuronal activity. The selectivity of the compounds against those ganglia-type receptors responsible for cardiovascular side effects is demonstrated by a lack of the ability of those compounds to activate nicotinic function of adrenal chromaffin tissue at concentrations greater than those required for modulation of CNS neuronal activity. Thus, administration of the compounds provides a therapeutic window in which treatment of certain CNS disorders is provided, and certain side effects are avoided. That is, an effective dose of the compound is sufficient to provide the desired effects upon the CNS, but is insufficient (i.e., is not at a high enough level) to provide undesirable side effects.

The pharmaceutical compositions are useful in the treatment of a variety of CNS disorders, including but not limited to neurodegenerative disorders, neuropsychiatric disorders, neurologic disorders, and addictions. The pharmaceutical compositions can be used to treat cognitive deficits (age-related and otherwise), attentional disorders and dementias (including but not limited to those due to infectious agents or metabolic disturbances); to provide neuroprotection; to treat convulsions and multiple cerebral infarcts; to treat mood disorders, compulsions and addictive behaviors; to provide analgesia; and to control inflammation (such as mediated by cytokines and nuclear factor kappa B) and treat inflammatory disorders. Among the disorders, diseases and conditions, that pharmaceutical compositions of the present invention can be used to treat, are: age-associated memory impairment, mild cognitive impairment, pre-senile dementia (early onset Alzheimer's disease), senile dementia (dementia of the Alzheimer's type), Lewy body dementia, vascular dementia, Alzheimer's disease, stroke, AIDS dementia complex, attention deficit disorder, attention deficit hyperactivity disorder, dyslexia, schizophrenia, schizophreniform disorder, schizoaffective disorder, Parkinsonism including Parkinson's disease, Pick's disease, Huntington's chorea, tardive dyskinesia, hyperkinesia, progressive supranuclear palsy, Creutzfeld-Jakob disease, multiple sclerosis, amyotrophic lateral sclerosis, epilepsy, depression, panic disorders, bipolar disorders, generalized anxiety disorder, obsessive compulsive disorder, rage outbursts, Tourette's syndrome, autism, drug and alcohol addiction, tobacco addiction, obesity, acute pain, neuropathic pain, inflammatory pain, ulcerative colitis, irritable bowel syndrome, cachexia, osteoarthritis, psoriasis, rheumatoid arthritis, endotoxaemia, sepsis, asthma, atherosclerosis and idiopathic pulmonary fibrosis.

Thus, the present invention relates to the salts mentioned above for use in therapy. The present invention further relates to the use of said salts, in the manufacture of a medicament for treatment of a central nervous system disorder. Also provided is a method for treatment of a central nervous system disorder, comprising administering to a mammal in need of such treatment, a therapeutically effective amount of the salt of the present invention. Further provided is a method for treatment of disorders selected from the group consisting of age-associated memory impairment, mild cognitive impairment, pre-senile dementia (early onset Alzheimer's disease), senile dementia (dementia of the Alzheimer's type), Lewy body dementia, vascular dementia, Alzheimer's disease, stroke, AIDS dementia complex, attention deficit disorder, attention deficit hyperactivity disorder, dyslexia, schizophrenia, schizophreniform disorder, and schizoaffective disorder. Even further provided is a method for treatment of disorders selected from the group consisting of dementia related to Alzheimer's Disease, attention deficit disorder, mild cognitive impairment and age associated memory impairment.

IV. PHARMACEUTICAL COMPOSITIONS

According to one embodiment of the present invention there is provided a pharmaceutical composition comprising as active ingredient a therapeutically effective amount of a salt form of (2S)-(4E)-N-methyl-5-[3-(5-isopropoxypyridin)yl]-4-penten-2-amine, in association with one or more pharmaceutically acceptable diluents, excipients and/or inert carriers.

The manner in which the compositions are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid; intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch or by powder injection). Although it is possible to administer the compositions in the form of a bulk active chemical, it is preferred to present each compound in the form of a pharmaceutical composition for efficient and effective administration. Exemplary methods for administering such compounds will be apparent to the skilled artisan. For example, the compositions can be administered in the form of a tablet, a hard gelatin capsule or as a time release capsule. The administration of the pharmaceutical compositions described herein can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical composition is administered can vary. Administration preferably is such that the active ingredients of the pharmaceutical composition interact with receptor sites within the body of the subject that effect the functioning of the CNS. More specifically, in treating a CNS disorder administration preferably is such so as to optimize the effect upon those relevant receptor subtypes, which have an effect upon the functioning of the CNS, while minimizing the effects upon muscle-type receptor subtypes.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to modulate the activity of relevant nicotinic receptor subtypes (e.g., modulate neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate relevant receptors to affect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular and ganglionic effects are observed.

Typically, the effective dose of compounds may require administering the compound in an amount of less than 5 mg/kg of patient weight. Often, the compounds may be administered in an amount from less than about 1 mg/kg patent weight to less than about 100 µg/kg of patient weight, and occasionally from about 10 µg/kg to less than 100 µg/kg of patient weight. The foregoing effective doses typically represent that amount administered as a single dose, or as one or more doses administered over a 24 hours period.

For human patients, the effective dose of the compounds may require administering the compound in an amount of at least about 1, but not more than about 1000, often not more than about 500 mg/24 hr./patient.

The compounds also can be administered in formulation compositions that incorporate other ingredients, such as those types of ingredients that are useful in formulating a diagnostic composition. Compositions useful as diagnostics can be employed as set forth in U.S. Pat. Nos. 5,853,696 to Elmalch et al. and 5,969,144 to London et al., the contents of which are hereby incorporated by reference.

The compounds can also be formulated and/or administered in combination with other therapeutic compounds, such as those used in the treatment and or prevention of CNS disorders.

U.S. Provisional Application Ser. No. 60/746,808 is incorporated herein by reference in its entirety.

V. EXAMPLES

The following examples are provided to illustrate the present invention, and should not be construed as limiting thereof. In these examples, all parts and percentages are by weight, unless otherwise noted.

Example 1

Determination of Binding to Relevant Receptor Sites

Binding of the compounds to relevant receptor sites was determined in accordance with the techniques described in U.S. Pat. No. 6,953,855 to Mazurov et al Inhibition constants (Ki values), reported in nM, were calculated from the IC50 values using the method of Cheng et al., *Biochem, Pharmacol.* 22:3099 (1973). Low binding constants indicate that the compounds of the present invention exhibit good high affinity binding to certain CNS nicotinic receptors.

Example 2

Synthesis of (2S)-(4E)-N-methyl-5-[3-(5-isopropoxypyridin)yl]-4-penten-2-amine (2S)-(4E)-N-Methyl-5-[3-(5-isopropoxypyridin)yl]-4-penten-2-amine was prepared according to the procedures described in PCT WO 99/65876 to Caldwell et al. and in U.S. application Ser. No. 11/270,018.

Example 3

Crystallization of (2S)-(4E)-N-methyl-5-[3-(5-isopropoxypyridin)yl]-4-penten-2-amine phosphate (2S)-(4E)-N-methyl-5-[3-(5-isopropoxypyridin)yl-4-penten-2-amine free base (452 mg) was dissolved in acetone (3.0 mL) and aqueous phosphoric acid (130 µL, >85%) was added. The resulting sticky precipitation was left overnight. The acetone was then evaporated and a small amount of n-heptane was added. The solvent was evaporated again. The solid was dried under vacuum to remove all solvent residues. Then, 2-propanol (2 mL) was added. After a few minutes, the material formed needle-shaped crystals. The slurry was left over night with stirring before the crystals were filtered off and dried. The crystalline material was used as seed crystals in later examples.

The melting point was determined by differential scanning calorimetry (DSC) at a rate of 10K/min. The phosphate salt has a melting point of 107.3° C. (onset), with a peak value of 108° C.

Example 4

Preparation of Phosphate Salt (2-Propanol as Solvent)

(2S)-(4E)-N-methyl-5-[3-(5-isopropoxypyridin)yl-4-penten-2-amine free base (829 mg) was dissolved in 2-propanol (4 mL) at 20° C. To the clear solution aqueous phosphoric acid was added (0.24 mL, >85%) and seed crystals from example 3 was added. No crystallization was obtained. After 1 hour the solvent was evaporated. A second portion of 2-propanol (4 mL) was added and the solid was slurried for a few minutes before the solvent was evaporated completely again. This evaporation procedure was repeated twice, first with 2-propanol (3 mL) followed by iso-octane (4 mL) until a dry sample was obtained. The resulting solid was slurried in 2-propanol (3 mL) over night with stirring. Then, the product was filtered off and dried under vacuum at 40° C. yielding approximately 0.85 g crystalline salt.

The following NMR data were obtained:

NMR: $^1$H (500 MHz, DMSO-d$_6$): 8.17 (1H, d), 8.09 (1H, d), 7.46 (1H, t), 6.46 (2H, m), 4.75 (1H, septet), 3.04 (1H, m), 2.63 (1H, m), 2.47 (3H, s), 2.38 (1H, m), 1.27 (6H, d), 1.18 (3H, d)

The ratio of acid to base is 1:1 in the salt.

NMR Abbrevations:
s singlet
d doublet
t triplet
m multiplet
DMSO: dimethyl sulfoxide The crystals were analyzed by XRPD and the results are tabulated below (Table 1).

TABLE 1

| Phosphate Salt XRPD | |
|---|---|
| Distance (Å) | Rel. Intensity |
| 18.6 | vs |
| 9.3 | s |
| 7.8 | vw |
| 7.1 | w |
| 6.7 | w |
| 6.5 | vw |
| 6.3 | vw |
| 6.2 | m |
| 6.1 | vw |
| 5.9 | w |
| 5.6 | w |
| 5.3 | w |
| 5.2 | vw |
| 5.1 | vw |
| 5.0 | vw |
| 4.83 | w |
| 4.77 | w |
| 4.69 | m |
| 4.59 | w |
| 4.53 | vw |
| 4.49 | m |
| 4.37 | m |
| 4.34 | vw |
| 4.25 | m |
| 4.21 | w |
| 4.14 | vw |
| 4.11 | vw |
| 4.07 | vw |
| 3.99 | m |
| 3.95 | vw |
| 3.92 | w |
| 3.76 | vw |
| 3.69 | vw |
| 3.65 | vw |
| 3.59 | w |
| 3.46 | m |
| 3.42 | vw |
| 3.36 | m |
| 3.25 | w |
| 3.18 | vw |
| 3.11 | m |
| 3.01 | vw |

TABLE 1-continued

| Phosphate Salt XRPD | |
|---|---|
| 2.99 | vw |
| 2.83 | vw |
| 2.72 | vw |
| 2.67 | vw |
| 2.34 | vw |

Definitions used:
% Relative intensity* — Definition
80-100 — vs (very strong)
30-80 — s (strong)
4-30 — m (medium)
2-4 — w (weak)
<2 — vw (very weak)

*The relative intensities are derived from diffractograms measured with variable slits.

Example 5

Preparation of Phosphate Salt (Acetone as Solvent, Followed by Evaporation)

(2S)-(4E)-N-methyl-5-[3-(5-isopropoxypyridin)yl-4-penten-2-amine free base (941 mg) was dissolved in acetone (5 mL) at room temperature and phosphoric acid (270 μl, >85%) was added. The resulting sticky precipitation was dried completely by evaporation. Then, acetone (5 mL) was added. The solid material started to crystallize and was slurried for 1 hour before more acetone was added (10 mL). The resulting slurry was left over night with stirring before it was filtered off and washed with acetone (2×2 mL). The product was dried at 40° C. under vacuum to yield 1.12 g crystalline (2S)-(4E)-N-methyl-5-[3-(5-isopropoxypyridin)yl-4-penten-2-amine phosphate corresponding to a yield of approximately 84%.

Example 6

Preparation of Phosphate Salt (Acetone as Solvent, without Evaporation)

(2S)-(4E)-N-methyl-5-[3-(5-isopropoxypyridin)yl-4-penten-2-amine free base (1.14 g) was dissolved in acetone (10 mL) at room temperature and phosphoric acid (200 μl, >85%) was added. Seed crystals from example 3 were added. Then a second portion of phosphoric acid (127 μl) was added. Crystallization started after a few minutes. Additional acetone (5 mL) was then added to dilute the slurry.

The resulting, thick slurry was left over night with stirring before it was filtered off and washed three times with acetone (in total 10 mL). The product was dried at 40° C. under vacuum to yield 1.17 g crystalline (25)-(4E)-N-methyl-5-[3-(5-isopropoxypyridin)yl-4-penten-2-amine phosphate corresponding to a yield of approximately 73%.

Example 7

Preparation of Phosphate Salt (Ethyl Acetate as Solvent, without Evaporation)

(2S)-(4E)-N-methyl-5-[3-(5-isopropoxypyridin)yl-4-penten-2-amine free base (910 mg) was dissolved in ethyl acetate (12 mL) at room temperature and phosphoric acid (260 μL, >85%) was added. A sticky lump was initially formed. Seed crystals from example 5 were added and gradually a slurry was formed. The slurry was left over night before it was filtered off and washed four times with ethyl acetate (4×2 mL). The product was dried at 40° C. under vacuum to yield 1.09 g crystalline (2S)-(4E)-N-methyl-5-[3-(5-isopropoxypyridin)yl-4-penten-2-amine phosphate corresponding to a yield of approximately 85%.

Example 8

Preparation of Phosphate Salt (Acetonitrile as Solvent, without Evaporation)

(2S)-(4E)-N-methyl-5-[3-(5-isopropoxypyridin)yl-4-penten-2-amine free base (1.06 g) was dissolved in acetonitrile (13 mL) at room temperature and phosphoric acid (305 µL, >85%) was added. Initially some sticky precipitation was formed. Then, seed crystals from example 7 were added. Crystallization started after a few minutes and the sample was left over night with stirring. Then, acetonitrile (3 mL) was added before it was filtered off and washed twice with acetonitrile (2×3 mL). The product was dried at 40° C. under vacuum to yield 1.47 g crystalline (2S)-(4E)-N-methyl-5-[3-(5-isopropoxypyridin)yl-4-penten-2-amine phosphate corresponding to a yield of approximately 98%.

Example 9

Crystallization of (2S)-(4E)-N-methyl-5-[3-(5-isopropoxypyridin)yl]-4-penten-2-amine edisylate (2S)-(4E)-N-methyl-5-[3-(5-isopropoxypyridin)yl-4-penten-2-amine free base (403 mg) was dissolved in 2-propanol (4 mL) at room temperature and 1,2-ethanedisulfonic acid (331 mg, 95%) was added. Initially, a clear solution was obtained but after a few minutes crystallization started spontaneously. The resulting slurry was left over night with stirring. The crystals were filtered off, washed with 2-propanol (2×1 mL) and dried at 50° C. under vacuum to yield 520 mg crystalline (2S)-(4E)-N-methyl-5-[3-(5-isopropoxypyridin)yl-4-penten-2-amine edisylate, corresponding to a yield of approximately 74%.

The melting point was determined by differential scanning calorimetry (DSC) at a rate of 10K/min. The edisylate salt has a melting point of 183.2° C. (onset), with a peak value of 184° C.

The ratio of acid to base is 1:1 in the salt.

NMR: $^1$H (500 MHz, DMSO-$d_6$): 8.57 (1H, d), 8.50 (1H, d), 8.5 (2H, m), 8.16 (1H, br t), 6.69 (2H, br t), 4.93 (1H, septet), 3.32 (1H, m), 2.73 (4H, s), 2.7 (1H, m), 2.60 (3H, br t), 2.5 (1H, m), 1.34 (6H, d), 1.25 (3H, d)

NMR Abbrevations:
br broad
s singlet
d doublet
t triplet
m multiplet

TABLE 2

| Edisylate Salt | |
| --- | --- |
| Distance (Å) | Rel. Intensity |
| 18.0 | w |
| 9.4 | m |
| 9.2 | m |
| 7.7 | w |
| 7.3 | m |
| 6.0 | w |
| 5.8 | w |
| 5.6 | m |
| 5.5 | w |

TABLE 2-continued

| Edisylate Salt | |
| --- | --- |
| 5.2 | w |
| 4.9 | w |
| 4.8 | vw |
| 4.7 | m |
| 4.6 | m |
| 4.6 | m |
| 4.44 | s |
| 4.33 | s |
| 4.27 | w |
| 4.19 | s |
| 4.11 | w |
| 3.95 | vw |
| 3.85 | vw |
| 3.80 | w |
| 3.76 | m |
| 3.66 | w |
| 3.63 | m |
| 3.61 | m |
| 3.51 | w |
| 3.37 | w |
| 3.35 | w |
| 3.26 | w |
| 3.24 | w |
| 3.21 | w |
| 3.18 | w |
| 3.12 | vw |
| 3.08 | w |
| 2.87 | vw |
| 2.77 | vw |
| 2.67 | vw |

Definitions used:

| % Relative intensity* | Definition |
| --- | --- |
| — | vs (very strong) |
| 60-100 | s (strong) |
| 20-60 | m (mediium) |
| 8-20 | w (weak) |
| <8 | vw (very weak) |

*The relative intensities are derived from diffractograms measured with variable slits.

Example 10

Crystallization of (2S)-(4E)-N-methyl-5-[3-(5-isopropoxypyridin)yl]-4-penten-2-amine edisylate (crystallization from acetone)

(2S)-(4E)-N-methyl-5-[3-(5-isopropoxypyridin)yl-4-penten-2-amine free base (786 mg) was dissolved in acetone (10 mL) at room temperature and 1,2-ethanedisulphonic acid (672 mg, 95%) was added. Initially, a sticky precipitation was formed. After seeding, the material started to crystallize. After 3 hours, more acetone (3 mL) was added. Then, the resulting slurry was left over night with stirring. The crystals were filtered off, washed with acetone (5 mL) and dried at 50° C. under vacuum to yield 1.05 g crystalline (2S)-(4E)-N-methyl-5-[3-(5-isopropoxypyridin)yl-4-penten-2-amine-edisylate, corresponding to a yield of approximately 76%.

Example 11

Crystallization of (2S)-(4E)-N-methyl-5-[3-(5-isopropoxypyridin)yl]-4-penten-2-amine edisylate (crystallization from acetonitrile)

(2S)-(4E)-N-methyl-5-[3-(5-isopropoxypyridin)yl-4-penten-2-amine (932 mg) was dissolved in acetonitrile (15 mL) at room temperature and 1,2-ethanedisulfonic acid (797 mg, 95%) was added. After seeding with material from example 10, it started to crystallize. Then, the resulting slurry was left over night with stirring. The crystals were filtered off, washed with ethyl acetate (2×2 mL) and dried at 40° C. under vacuum to yield 1.23 g crystalline (2S)-(4E)-N-methyl-5-[3-(5-isopropoxypyridin)yl-4-penten-2-amine edisylate corresponding to a yield of approximately 75%.

Example 12

Preparation of amorphous citric acid salt of (2S)-(4E)-N-methyl-5-[3-(5-isopropoxypyridin)yl-4-penten-2-amine (2S)-(4E)-N-methyl-5-[3-(5-isopropoxypyridin)yl-4-penten-2-amine free base (403 mg) was dissolved in 2-propanol (4 mL) and citric acid monohydrate (363 mg) was added. A sticky precipitation was formed which was dried by evaporation. The resulting material was completely dissolved in ethanol (4 mL) and evaporated to dryness again. A solid, amorphous material was formed. The substance was slurried in 2-propanol (2 mL) and evaporated to dryness. The substance was then slurried in methyl isobutyl ketone (MiBK, 3 mL). The solvent was evaporated completely and the substance was slurried in acetone (8 mL). Finally, the acetone was evaporated and an amorphous substance was obtained after drying under vacuum at room temperature.

Example 13

Preparation of orotic acid (uracil-6-carboxylic acid) salt of (2S)-(4E)-N-methyl-5-[3-(5-isopropoxypyridin)yl-4-penten-2-amine Orotic acid (0.663 g, 4.25 mmol) was added to a solution of (2S)-(4E)-N-methyl-5-(3-(5-isopropoxypyridin)yl)-4-penten-2-amine (1.00 g, 4.27 mmol) in absolute ethanol (6 mL). The mixture was stirred and heated to near reflux, dissolving almost all solids. The solution was concentrated via rotary evaporation to an off-white foam. The residue was dissolved in ethyl acetate (7.8 mL) and absolute ethanol (1.8 mL), assisted by heating. The resulting solution was cooled to 5° C., and additional ethyl acetate (6.8 mL) and ethanol (0.8 mL) were added. The mixture was heated, and the solution was allowed to cool to ambient temperature. The resulting mixture, containing fine, white solids was cooled to 5° C. for 48 hours. The solids were filtered, washed with cold ethyl acetate (3×3 mL) and dried under vacuum at 40° C. for 22 hours, followed by further drying at 50° C. for 3 hours to afford 1.523 g (91.4%) of a white powder, m.p. 128.5-132° C. (Fisher-Johns hot stage). Elemental analysis and NMR were both consistent with a 1:1 stoichiometry.

Calc'd for $C_{14}H_{22}N_2O \cdot C_5H_4N_2O_4$: C, 58.45%; H, 6.71%; N, 14.35%.

Found: C, 58.63%; H, 6.67%; N, 14.42%.

The following NMR data were obtained:

NMR: $^1$H (300 MHz, $D_2O$): 8.16 (1H, d), 8.10 (1H, d), 7.45 (1H, t), 6.62 (1H, d), 6.35 (1H, m), 6.15 (1H, s), 4.76 (1H, septet), 3.46 (1H, m), 2.73 (3H, s), 2.64 (2H, m), 1.38 (3H, d), 1.36 (6H, d).

Example 14

Preparation of R-mandelic acid salt of (2S)-(4E)-N-methyl-5-[3-(5-isopropoxypyridin)yl-4-penten-2-amine R-Mandelic acid (0.207 g, 1.35 mmol) was added to a solution of (2S)-(4E)-N-methyl-5-(3-(5-isopropoxypyridin)yl)-4-penten-2-amine (0.319 g, 1.35 mmol) in isopropanol (2 mL). The mixture was swirled to dissolve the mandelic acid, and the isopropanol was removed by rotary evaporation. The oily residue would not crystallize from various mixtures of acetone and hexane, so these solvents were removed by rotary evaporation. The residue would not crystallize from mixtures of ethyl acetate and diethyl ether, so the mixture was again concentrated by rotary evaporation. This residue was placed in the refrigerator (~5° C.) for 72 hours. The resulting solid mass was broken up and dried under a stream of nitrogen gas. This was recrystallized from hexane/acetone to give 487 mg (93%) of needle-like crystals (m.p. 87-89° C.; Fisher-Johns hot stage). A $^1$H NMR indicated a 1:1 stoichiometry.

The following NMR data were obtained:

NMR: $^1$H (300 MHz, $D_2O$): 8.17 (1H, d), 8.09 (1H, d), 7.45 (1H, t), 7.43 (5H, m), 6.62 (1H, d), 6.35 (1H, m), 5.00 (1H, s), 4.76 (1H, septet), 3.43 (1H, m), 2.73 (3H, s), 2.64 (2H, m), 1.38 (3H, d), 1.36 (6H, d).

Example 15

Preparation of sulphate, 1,5-naphtalenedisulfonic acid (1:1 and 2:1), D-aspartic acid (1:2) and lysine monohydrochloride (1:1 and 1:2) salts of (2S)-(4E)-N-methyl-5-[3-(5-isopropoxypyridin)yl-4-penten-2-amine All these salts may be prepared in a similar manner:

(i) The free base or a solution of the free base in a suitable solvent is mixed with any of the acids in pure form or as a solution of any of the acids in a suitable solvent (typically 0.5 to 1 equivalents of the acid), (iia) cooling the resulting salt solution if necessary to cause precipitation, or (iib) adding a suitable anti-solvent to cause precipitation, or (iic) evaporating the first solvent and adding and new solvent and repeating either steps (iia) or step (iib), and (iii) filtering and collecting the salt.

The foregoing is illustrative of the present invention and is not to be construed as limiting thereof. The invention is defined by the following claims, with equivalents of the claims to be included therein.

The invention claimed is:

1. The phosphoric acid salt of (2S)-(4E)-N-methyl-5-[3-(5-isopropoxypyridin)yl]-4-penten-2-amine having an X-ray powder diffraction pattern with specific peaks at d-values at 18.6, 9.3, 4.25, 3.99, and 3.11 Å, and/or essentially as defined in Table 1.

2. The edisylate salt of (2S)-(4E)-N-methyl-5-[3-(5-isopropoxypyridin)yl]-4-penten-2-amine having an X-ray powder diffraction pattern with specific peaks at d-values at 5.6, 4.33, 4.19, and 3.76 Å, and/or essentially as defined in Table 2.

3. A pharmaceutical composition comprising as active ingredient a therapeutically effective amount of the salt of claim 1, in association with one or more pharmaceutically acceptable diluents, excipients and/or inert carriers.

4. A pharmaceutical composition comprising as active ingredient a therapeutically effective amount of the salt of claim 2, in association with one or more pharmaceutically acceptable diluents, excipients and/or inert carriers.

* * * * *